United States Patent [19]

Okisaka et al.

[11] Patent Number: 5,709,901
[45] Date of Patent: Jan. 20, 1998

[54] MEAT MODIFIER AND FOOD MEAT OR MEAT PRODUCT PROCESSED WITH SAME

[75] Inventors: Koichi Okisaka; Manabu Toi; Yoko Sakurai; Yutaka Shoga; Hirofumi Takigawa, all of Ibaraki, Japan

[73] Assignee: Kao Corporation, Tokyo, Japan

[21] Appl. No.: 514,230

[22] Filed: Aug. 11, 1995

[30] Foreign Application Priority Data

Aug. 17, 1994 [JP] Japan ............................... 6-216660
Apr. 28, 1995 [JP] Japan ............................... 7-106272

[51] Int. Cl.⁶ .................................................. A23D 7/01
[52] U.S. Cl. ............................ 426/611; 426/601; 426/602; 426/612
[58] Field of Search .................................. 426/601, 602, 426/611, 612

[56] References Cited

U.S. PATENT DOCUMENTS 4,229,480  10/1980  Supps et al. .
5,137,743   8/1992  Zaks et al. ............................ 426/602

FOREIGN PATENT DOCUMENTS 0 658315  6/1995  European Pat. Off. .
2639809   3/1977  Germany .
126981    8/1977  Germany .

OTHER PUBLICATIONS

Database WPI, Derwent Publications, AN–84–008090, JP-A-58-201964, Nov. 25, 1983.
Database WPI, Derwent Publications, AN–95–307120, JP-A-07-203905, Aug. 8, 1995.
Database WPI, Derwent Publications, AN-83-714896, JP:-A 54-062356, May 19, 1979.
Patent Abstracts of Japan, vol. 15, No. 508 (C-0897), Dec. 24, 1991, JP-A-3 224464, Oct. 3, 1991.
Journal of Bacteriology, vol. 172, No. 2, pp. 1019–1023, Feb. 1990, G. Rufo, Jr., et al., "Isolation and Characterization of a Novel Extracellular Metalloprotease from Bacillus Subtilis".
Chemiker–Zeitung, vol. 98, No. 11, pp. 539–548, Nov. 1974, Von Wolfgang Schreiber, et al., "Production and Use of Microbial Proteases".

*Primary Examiner*—Donald E. Czaja
*Assistant Examiner*—Choon P. Koh
*Attorney, Agent, or Firm*—Oblon, Spivak, McClelland, Maier & Neustadt, P.C.

[57] ABSTRACT

The present invention provides an ester composition which can tenderize a stringy hard meat such as beef from abroad to a proper tenderness, the processing time, etc. and a meat tenderizer comprising said ester composition and protease without giving a special control over the amount of an enzyme. The present invention also provides a meat modifier which can provide a tender, juicy and less stringy meat that can be easily served and a food meat or meat product processed with such a meat modifier. A meat modifier is also provided, comprising an ester composition of a $C_{12-22}$ saturated or unsaturated fatty monoglyceride with succinic acid or diacetyltartaric acid having an acid value of from 30 to 120. The present invention provides a meat modifier comprising the ester composition and a metalloprotease, which no longer causes round to be tenderized after 24 hours of storage at a temperature of 20° C. with said metalloprotease kept in contact therewith in a proportion of 300 units per 10 g in enzyme equivalence.

7 Claims, 2 Drawing Sheets

MEAT MODIFIER AND FOOD MEAT OR MEAT PRODUCT PROCESSED WITH SAME

FIELD OF THE INVENTION

The present invention relates to a meat modifier and a food meat or meat product processed with said meat modifier. More particularly, the present invention relates to a meat modifier which can provide a meat that remain tender and juicy even when grilled, fried or otherwise cooked and thus can be served with a good flavor and taste and a food meat or meat product processed with said meat modifier.

BACKGROUND OF THE INVENTION

As Japan's beef market has been opened to foreign countries, Japan has been able to buy an abundant beef for lower price. Imported beef contains less fat than Japanese-made beef and thus is healthy but is disadvantageous in that it is generally tough. Taking into account the fact that most Japanese people like a relatively tender meat and the population of the aged people has grown, the development of a meat modifier for properly tenderizing a meat has been desired.

As a meat tenderizer there has been heretofore used a protease. One of the most frequently used meat tenderizers is papain derived from papaya. However, papain is disadvantageous in that it is hard to control in tenderization (i.e., control over the progress of tenderization to a proper level) and its use is restricted by the added amount thereof and the processing time. In fact, papain was subjected to meat tenderization test. As a result, even when used in an amount as extremely small as 0.1 based on the weight of the meat to be tested, this enzyme overtenderized the meat within 1 hour at room temperature and in a period of time as short as 24 hours at a temperature as low as 4° C. The meat thus overtenderized was too unsavory to be served. This is because proteases derived from plants have a low substrate specificity. Other proteases such as bromelin derived from pineapple and actinidin derived kiwi fruit exhibit similar tenderizing properties.

On the other hand, a method has been proposed which comprises the specific decomposition of a connective tissue in a meat with elastase, which has a high substrate specificity, to tenderize the meat (JP-A-4-197156 (The term "JP-A" as used herein means an "unexamined published Japanese patent application"), JP-A-5-276899). However, this approach is disadvantageous in that elastase is hard to produce and must be used in a relatively large amount and requires a prolonged processing time to exert desired effects as compared with the foregoing proteases. It has also been point out that elastase cannot tenderize a meat sufficiently even if the added amount thereof and the processing time are increased (JP-A-6-169729). When a meat was actually processed with a reagent grade elastase, the meat was slightly tenderized, but the tenderness thus obtained was insufficient.

There are many meat foods obtained by cooking beast meats such as beef and pork, fowl meats such as chicken and duck or fish such as saurel and white fish. It is desirable that these meats should be served in a properly tender form rich with a juice as a delicious component (juicy) regardless of how to cook the meat, e.g., baking, frying. In particular, tenderness and juiciness are important factors of deliciousness for meat foods made of a relatively large piece of unprocessed beast or fowl meat such as steak and fried cutlet or molded foods made of minced pieces of these meats such as hamburger. However, these meats, particularly with a certain size, generally tend to harden and lose juice when cooked. If the meat quality is not too good, the meat tends to harden as well as become more stringy, further worsening its taste. It has thus been desired to improve these meats such that they can be well served tender with a good taste.

As meat modification methods for tenderizing a meat or enhancing the preservability of a meat there have heretofore been known a method which utilizes an organic acid monoglyceride (e.g., acetylated monoglyceride) (JP-A-49-20353), a method which utilizes an activator such as lecithin (JP-A-54-62356, JP-A-4-148663), a method which utilizes salts (JP-A-4-36167, JP-A-61-23862), and a method which utilizes an enzyme (JP-A-4-278063, JP-A-5-7476, JP-A-5-252911).

In order to obtain a puffy and/or juicy molded food made of minced meat, many methods have been proposed. For example, JP-A-54-54359 discloses a method which comprises mixing sodium bicarbonate, an acidic agent and a stabilizer with a molded food. JP-A-1-228427 discloses a method which utilizes a composition made of an edible oil and fat, a natural wax and an edible surface active agent. JP-A-5-103632 discloses a method which comprises mixing an oil-in-water type emulsion with a molded food. Further, JP-A-5-176721 discloses a method which comprises mixing an oil-in-water-in-oil type emulsion with a molded food.

However, studies made by the inventors show that these methods leave something to be desired.

SUMMARY OF THE INVENTION

It is therefore an object of the present invention to provide an ester composition which can tenderize a stringy hard meat such as beef from abroad to a proper tenderness without giving a special control over the amount of an enzyme, the processing time, etc. and a meat modifier comprising said composition and protease.

It is another object of the present invention to provide a meat modifier which can provide a tender, juicy and less stringy meat that can be easily served and a food meat or meat product processed with such a meat modifier.

DETAILED DESCRIPTION OF THE INVENTION

A meat pickled in miso is a well-known meat product which can remain tasty and tender. The inventors paid their attention to protease contained in miso and had an idea that this protease takes part in the tenderization of the meat. The inventors then investigated protease-producing strains in various miso's for preserving meats. As a result, bacilli were found which produce a novel protease that can properly tenderize a meat but does not overtenderize the meat as papain even if the added amount thereof or the processing time is increased. Thus, the present invention has been worked out.

The present invention utilizes a metalloprotease which no longer causes round to be tenderized after 24 hours of storage at a temperature of 20° C. with said metalloprotease kept in contact therewith in a proportion of 300 units per 10 g in enzyme equivalence.

While studies were being made to accomplish the foregoing objects of the present invention, the inventors found that meats, particularly animal meats and fowl meats, contain a relatively large amount of such a corrective tissue (collagen) as contained in tendon, and this corrective tissue shrinks and agglutinates when the meat is cooked, giving a firm and hard meat. It was also found that an ester composition of a monoglyceride or diglyceride with a polycarboxylic acid can be very advantageously added to inhibit the shrinkage of such a protein and hence obtain a tender meat. The inventors then applied this technique for a patent (JP-A-5-343815).

It was further found that the combined use of such an ester composition and protease can provide enhancement in the tenderization of a meat as well as in the taste thereof. This technique, too, was applied for a patent (JP-A-6-131456).

The present invention has been worked out as a result of further achievement of the foregoing studies. The inventors found that among the foregoing ester compositions a specific ester composition comprising a monoglyceride containing a fatty acid having a specified number of carbon atoms and a specific polycarboxylic acid and having an acid value falling within a specified range can exert a remarkable effect of improving the flavor of a meat and an effect of keeping the meat fairly tender and juicy. Among there ester compositions, an ester composition having free acids in less amount is particularly preferred. Thus, the present invention has been worked out.

Free acids are free succinic acids which are contained in the esterified composition of monoglyceride with succinic acid, and free acids of diacetyltartaric acid, monoacetyltartaric acid, tartaric acid or acetic acid which are contained in the esterified composition of monoglyceride with diacetyltartaric acid. The ester composition in the meat modifier of the present invention contains free acids in an amount of 1.5% by weight or less.

The present invention concerns a meat modifier comprising an ester composition of a $C_{12-22}$ saturated or unsaturated fatty monoglyceride with succinic acid having an acid value of from 30 to 120 or an ester composition of $C_{12-22}$ saturated or unsaturated fatty monoglyceride with diacetyltartaric acid having an acid value of from 30 to 120 and a food meat or meat product processed with such a meat modifier.

Preferred embodiments of the meat tenderizer of the present invention will be given below.

(1) The $C_{12-22}$ saturated or unsaturated fatty acid to be contained in the ester composition of a $C_{12-22}$ saturated or unsaturated fatty monoglyceride with succinic acid or diacetyltartaric acid comprises one or more of lauric acid, myristic acid, palmitic acid, stearic acid, oleic acid, linoleic acid and behenic acid, preferably myristic acid, palmitic acid, stearic acid and oleic acid.

The present invention may include some of ester compositions of a monoglyceride with a polycarboxylic acid such as saturated dicarboxylic acid (e.g., oxalic acid, malonic acid, succinic acid, glutaric acid, adipic acid, pimelic-acid, suberic acid, azelaic acid), unsaturated dicarboxylic acid (e.g., maleic acid, methylmaleic acid, fumaric acid, methylfumaric acid), hydroxycarboxylic acid (e.g., malic acid, tartaric acid, citric acid) and carboxylic acid obtained by replacing the hydroxyl group in hydroxycarboxylic acid by acetic acid or by entirely or partially esterifying the foregoing carboxylic acid such as oxalic acid.

(2) The meat modifier is preferably used in an amount of from 0.05 to 5% by weight (more preferably from 0.1 to 3% by weight, particularly from 0.3 to 2% by weight) based on the weight of the meat to be modified in ester equivalence.

(3) The food meat is included in cooked or cookable food products such as frozen food, refrigerated food and retorted food.

The meat modifier of the present invention will be further described hereinafter.

The meat modifier of the present invention comprises an ester composition of a $C_{12-22}$ saturated or unsaturated fatty monoglyceride with succinic acid having an acid value of from 30 to 120 (hereinafter occasionally referred to as "succinic ester composition") or an ester composition of a $C_{12-22}$ saturated or unsaturated fatty monoglyceride with diacetyltartaric acid having an acid value of from 30 to 120 (hereinafter occasionally referred to as "diacetyltartaric ester composition").

The fatty acid residue constituting the monoglyceride in the succinic ester composition is a $C_{12-22}$ (preferably $C_{14-18}$) saturated or unsaturated fatty acid residue. The fatty acid residue constituting the monoglyceride in the acetyltartaric ester composition is a $C_{12-22}$ (preferably $C_{14-18}$) saturated or unsaturated fatty acid residue.

In the ester composition obtained by the reaction of the foregoing monoglyceride with succinic acid or diacetyltartaric acid, the proton in the carboxylic acid, which does not participate in the reaction, may occur in the free state or may form a salt. Examples of the paired ions constituting the salt include potassium, sodium, calcium, magnesium and aluminum ions.

The ester composition of the present invention may be obtained in various kinds of structures depending on the molar amount of the monoglyceride to be reacted with succinic acid or diacetyltartartic acid, the kind of the fatty acid residue, etc. In general, the ester composition of the present invention is obtained in the form of a mixture of these structures. For example, the succinic ester composition consists of a succinic ester composition (monomer) represented by the following formula (1) and a succinic ester composition (polymer) represented by, e.g., the following formula (2), the molar ratio of the monomer to the polymer being preferably not less than ¼:

(1)

(2)

wherein n represents an integer of not less than 2. The molar ratio of the monomer to the polymer may be 90:10 to 1:4. The molar ratio of the monomer to the polymer may also be 90:10 to 30:70.

Similarly, the diacetyltartaric ester composition consists of a diacetyltartaric ester composition (monomer) represented by the following formula (3), and a diacetyltartaric ester composition (polymer) represented by, e.g., the following formula (4):

(3)

(4)

wherein n represents an integer of not less than 2.

In the case of succinic ester composition, if the molar ratio of the monomer to the polymer falls below ¼, i.e., the molar ratio of the monomer is relatively large, it gives a tendency for the effect of tenderizing meat to be strong, though the effect can be sufficiently obtained when n =2 to 4.

In the present invention, the amount of free acids in the ester composition can be controlled by the following methods:

1) A method which comprises distilling an ester composition produced by an ordinary method under reduced pressure at a temperature of from 100° C. to 180° C. over from 1 to 5 hours to distill off the unreacted succinic acid or diacetyltartaric acid;

2) A method which comprises washing an ester composition produced by an ordinary method with a large amount of water to remove the unreacted succinic acid or diacetyltartaric acid away into a water phase;

3) A method which comprises reacting a monoglyceride with succinic acid or diacetyltartaric acid in a molar ratio of not less than 1:1; and 4) A method which comprises distilling off water in the reaction system of a monoglyceride with succinic acid or diacetyltartaric acid to reduce the amount of unreacted succinic acid or diacetyltartaric acid.

The use of a succinic ester composition or diacetyltartaric ester composition having an amount of free acids reduced by the foregoing method can remarkably exert the effect of the present invention.

The meat modifier of the present invention may comprise other arbitrary components. In particular, the meat modifier of the present invention preferably comprises protease contained therein to exert an enhanced effect of tenderizing meat. The protease employable in the present invention is not specifically limited. As the protease there may be used any protease produced from various origins. Examples of these proteases employable in the present invention include those derived from vegetables such as papain and bromelin, those derived from animal such as pancreas extract, and those derived from microorganisms such as mold. These proteases may be used singly or in combination. Preferred among these proteases are those derived from koji and those derived from bacillus.

Preferred embodiments of the protease used in the present invention will be given below.

(1) A metalloprotease which tenderizes a 5-mm thick round in such a manner that the shear force value of the round thus tenderized is from 25% to 65% (particularly from 30% to 50%) of that of the untenderized round; and (2) A metalloprotease which tenderizes a 15-mm thick round in such a manner that the shear force value of the round thus tenderized is from 30% to 70% (preferably from 40% to 70%, particularly from 40% to 60%) of that of the untenderized round.

The metalloprotease of the present invention and the meat tenderizer comprising the metalloprotease will be further described hereinafter.

The metalloprotease of the present invention is a protease which can properly tenderize a meat as mentioned above. The metalloprotease of the present invention does not overtenderize a meat as the conventional proteases even if the amount of the enzyme used and the processing (functioning) time are increased. The metalloprotease of the present invention is not specifically limited so far as it exhibits such properties. Examples of the metalloprotease which can be preferably used in the present invention include proteases obtained from a culture of a bacillus strain (e.g., KSM-PF1, KSM-PF2).

The microorganisms which produce proteases having the foregoing properties are termed "Bacillus sp. KSM-PF1" and "Bacillus sp. KSM-PF2", respectively. These microorganisms were deposited under Budapest Treaty with National Institute of Bioscience and Human-Technology, Agency of Industrial Science and Technology as accession Nos. BP-5190 and BP-5197, respectively. These strains have the following mycological properties:

| | Microbiological properties | |
|---|---|---|
| | KSM-PF1 | KSM-PF2 |
| (A) Morphological properties | | |
| a) Shape of cell | Bacillus | Bacillus |
| Size of cell | 0.6–0.8 μm × 1.2–2.0 μm | 0.8–1.0 μm × 1.2–2.5 μm |
| b) Polymorphism | None | None |
| c) Motility | Yes (peritrichous flagella) | Yes (peritrichous flagella) |
| d) Spore | 0.8–1.0 μm × 1.2–1.6 μm Ellipsoidal, center and quasi end | 1.0–1.2 μm × 1.4–2.0 μm Ellipsoidal, center and quasi end |
| e) Gram stain | Positive | Positive |
| f) Acid fastness | Negative | Negative |
| g) Growth form on piate bouillon agar | Circle, smooth surface | Circle, some wrinkle on surface |
| h) Growth form on slant bouillon agar | Irregular leave-shaped, smooth surface | Irregular leave-shaped, some wrinkle on surface |
| i) Culture in bouillon | Grown well, uniformly turbid | Grown well, pellicle formed |
| j) Stab culture in gelatin | Grown well, liquefied | Grown well, liquefied |
| k) Litmus milk | Peptonized, coagulated | Peptonized, not coagulated |
| (B) Physiological properties | | |
| a) Reduction of nitrate | Positive | Positive |
| b) Denitrification reaction | Negative | Negative |
| c) MR test | Negative | Negative |
| d) VP test | Positive | Positive |
| e) Production of indole | Negative | Negative |
| f) Production of hydrogen sulfide | Negative | Negative |
| g) Hydrolysis of starch | Negative | Negative |
| h) Utilization of citric acid | Positive | Positive |
| i) Utilization of inorganic nitrogen source | Nitrate and ammonium salt are utilized | Nitrate and ammonium salt are utilized |
| j) Dye-producing properties | Negative | Negative |
| k) Urease | Negative | Negative |
| l) Oxidase | Positive | Positive |
| m) Catalase | Positive | Positive |

-continued

| Microbiological properties | | |
|---|---|---|
| n) Growth temperature range | 15° C.–50° C. | 17° C.–55° C. |
| o) Growth pH range | 5.0–10.0 | 5.5–9.5 |
| p) Behavior with oxygen | Aerobic | Aerobic |
| q) OF test | F type | O type |
| r) Fastness to sodium chloride | 7.5% | 10% |
| s) Production of acid and gas from sugar | | |

| Kind of sugar | KSM-PF1 | KSM-PF2 |
|---|---|---|
| D-ribose | + | + |
| L-arabinose | + | + |
| D-xylose | + | + |
| D-fructose | + | + |
| D-glucose | + | + |
| D-mannose | + | + |
| D-galactose | + | + |
| Maltose | + | + |
| Sucrose | + | + |
| Lactose | + | + |
| Trehalose | + | + |
| Starch | + | − |
| Sorbitol | + | + |
| Inositol | + | + |
| Mannitol | + | + |
| Glycerin | + | + |
| Dextrin | + | − |
| Raffinose | + | − |

Gas is not produced from these sugars.

The foregoing microbiological properties were reviewed in accordance with a method described in "Bergey's Manual of Systematic Bacteriology", Williams & Wilkins, 1986. As a result, a conclusion was drawn that it is reasonable to classify KSM-PF1 and KSM-PF2 as *Bacillus pumilus* and *Bacillus subtilis*, respectively. However, KSM-PF1 differs from *Bacillus pumilus* in that it cannot grow at a temperature of 10° C. and reduces nitrates. KSM-PF2 differs from *Bacillus subtilis* in that it can grow at a temperature of 55° C. Further, these strains also differs from other known strains.

In order to obtain a metalloprotease of the present invention from the foregoing strains, the foregoing strains may be inoculated in a proper growth medium, and then cultured in accordance with an ordinary method.

As the growth medium employable herein there may be used any growth medium which is used for the culture of ordinary microorganisms and which allows the foregoing strains to grow. The growth medium preferably comprises assimilable carbon and nitrogen sources in a proper amount.

These carbon and nitrogen sources are not specifically limited. Examples of the carbon source include arabinose, xylose, glucose, glycerin, blackstrap molasses and invert sugar which can be assimilated with both KSM-PF1 and KSM-PF2, and assimilable organic acids such as acetic acid. Examples of the nitrogen source include corn gluten meal, soy bean powder, corn steep liquor, Casamino acid, yeast extract, farmer media, sardine meal, meat extract, peptone, hypro, saurel power, corn meal, soybean meal, coffee grounds, cottonseed oil cake, cultivator, amiflex, ajipron, zest, and ajix. Further, an inorganic salt such as salt of phosphoric acid, $Mg^{2+}$, $Ca^{2+}$, $Mn^{2+}$, $Zn^{2+}$, $Co^{2+}$, $Na^+$ and $K^+$ may be contained in the growth medium. If necessary, an inorganic or organic nutritive source may be contained in the growth medium in a slight amount.

The collection and purification of the metalloprotease as the desired substance produced from the culture can be effected in accordance with the ordinary method for the collection and purification of an enzyme. In some detail, the culture is subjected to centrifugation or filtration to separate the strain therefrom. The culture filtrate can then be subjected to an ordinary separation process such as salting-out, isoelectric point sedimentation and solvent sedimentation (e.g., methanol, ethanol, isopropyl alcohol, acetone) to cause the precipitation of protein or concentrated by ultrafiltration to obtain the desired metalloproteases.

The activity of the proteases obtained from the strain (hereinafter, protease obtained from the strain KSM-PF1 will occasionally be simply referred to as "PF-1", and protease obtained from the strain KSM-PF2 will occasionally be simply referred to as "PF-2") is inhibited by ethylenediaminetetraacetic acid (EDTA), which is an inhibitor of metalloproteases, but is not inhibited by diisopropylfluorophosphoric acid (DFP) or phenylmethanesulfonylfluoride (PMSF), which is an inhibitor of serine proteases, monoiodoacetic acid, dithiothreitol or leupeptine, which is an inhibitor of cysteine proteases, or pepstatin, which is an inhibitor of aspartic proteases. Thus, both the two proteases can be identified as metalloproteases.

The metalloprotease of the present invention is an enzyme which no longer causes round to be tenderized after 24 hours of storage at a temperature of 20° C. with said metalloprotease kept in contact therewith in a proportion of 300 enzymatic units per 10 g. In other words, the metalloprotease of the present invention can tenderizes a meat to a predetermined tenderness and then exerts little or no tenderizing effect with time even if the amount of the enzyme to be used or the processing time (time during which it comes in contact with the meat) is increased. The metalloprotease of the present invention preferably finishes tenderization within 24 hours (preferably within 10 hours) after the initiation of tenderization. For example, the foregoing protease PF-2 finishes tenderization within from 6 to 7 hours after the initiation of tenderization. The protease PF-1 finishes tenderization within from 15 to 20 hours after the initiation of tenderization.

The metalloprotease of the present invention preferably tenderizes round in such a manner that the shear force value of the round thus tenderized is from 20% to 70% (preferably from 25% to 65%, particularly from 30% to 50% of that of the untenderized round (round which has not been processed with the metalloprotease of the present invention) when the round has a thickness of 5 mm. The shear force value as defined herein is determined by subjecting the meat sample to cutting by a meat shear (Warner Bratzler Type 3000, available from Warner Bratzler Corp.). The meat sample is obtained by subjecting round to enzymatic processing at a temperature of 20° C., and then grilled-the round thus processed on both sides thereof at 200° C. (grilled on one side for 1 minute and one the other side for 45 seconds).

The metalloprotease of the present invention also preferably tenderizes round in such a manner that the shear force value of the round thus tenderized is from 30% to 70% (preferably from 40% to 70%, particularly from 40% to 60%) of that of the untenderized round (round which has not been processed with the metalloprotease of the present invention) when the round has a thickness of 15 mm. In this case, too, the shear force value is as defined above.

The meat tenderizer can be used as it is in the form of the enzyme solution thus obtained. In order to raise the specific activity of the meat tenderizer, the enzyme solution may be concentrated and purified by an ordinary method before use.

The enzyme solution may then be lyophilized so that it can be used in the form of powder. The enzyme solution thus lyophilized can maintain its enzymatic activity over a prolonged period of time. The enzyme solution thus lyophilized can find wide application. For example, such an enzyme powder can be used in admixture with other seasonings.

The meat tenderizer of the present invention can be applied to various kinds of meats. Examples of these meats include meat of birds and beasts such as beef, pork and chicken, and fish meat. In particular, the meat tenderizer of the present invention can be effectively applied to a stringy hard meat such as round, shoulder and other relatively low quality meats.

The amount of the meat tenderizer of the present invention to be used depends on the kind and added amount of the enzyme used. It is normally from 3 to 30 units, preferably from 5 to 10 units per g of meat in enzyme equivalence. In particular, the amount of the meat tenderizer comprising the foregoing protease PF-1, which can be preferably used in the present invention, is normally from 3 to 30 units, preferably from 10 to 30 units per g of meat in enzyme equivalence. The amount of the meat tenderizer comprising the foregoing protease PF-2 is normally from 3 to 30 units, preferably from 3 to 10 units per g of meat in enzyme equivalence.

Other examples of other arbitrary components include starch, protein, sugar, and seasoning.

The meat modifier of the present invention may be in any form such as liquid, paste and powder but is preferably in the form of liquid or powder from the standpoint of handleability, preservability, etc. If the meat modifier of the present invention is used in the form of liquid, it is preferably in the form of solution or dispersion in water or an aqueous liquid or in the form of solution or dispersion in a fatty oil.

If the meat modifier of the present invention is used in the form of powder, the foregoing arbitrary component such as starch may be used. For example, if the ester composition thus obtained is liquid, such an arbitrary component may be contained in the ester composition and then sprayed or treated otherwise to be formed into powder.

The meat modifier of the present invention may be used to advantage in such a manner that it is brought into direct contact with the meat to be modified, though depending on the shape of the meat or how the meat is cooked. When a relatively large meat such as steak meat is used, the powdered modifier may be directly applied to or sprayed over the meat to advantage. When a minced meat is used, the powdered modifier of the present invention can be advantageously added to the meat during the production of a molded food from the minced meat so that it is brought into direct contact with the minced meat.

Typical examples of the form of the modifier to be used in the cook of meat will be given below.

(1) To be contained in a powder base such as flour and powdered seasoning;
(2) To be contained in a cooking liquid food fatty oil such as soybean oil and corn oil;
(3) To be contained in a plastic fatty oil such as refined lard and shortening;
(4) To be contained in a W/O emulsion composition such as margarine;
(5) To be contained in an O/W emulsion composition; and
(6) To be contained in a liquid seasoning such as soup stock and sauce The meat modifier of the present invention is preferably used in an amount of from 0.05 to 5% by weight, more preferably from 0.1 to 3% by weight, particularly from 0.3 to 2% by weight based on the weight of the meat to be modified in ester equivalence.

The foregoing protease powder is preferably used in an amount of from 0.001 to 5% by weight, more preferably from 0.005 to 3% by weight, particularly from 0.01 to 1% by weight based on the weight of the meat to be modified.

In the meat modifier of the present invention, the mixing ratio of ester composition to protease by weight is preferably from 100:1 to 1:10, more preferably from 10:1 to 1:2.

The meat modifier of the present invention exerts it effect when a meat such as beef, pork and lamb, a meat of fowl such as chicken, turkey, duck and goose or fish such as saurel, salmon, cod and flatfish is cooked. The meat modifier of the present invention exerts a great effect particularly on beast meat and fowl meat. The position of the body on which the meat modifier of the present invention can exert its effect most effectively is a relatively tough protein-rich position such as shoulder and round. The meat form on which the meat modifier of the present invention can exert its effect most effectively is the piece of meat as mentioned above (e.g., chop, thin or fine slice). The meat modifier of the present invention can also exert its effect on the foregoing molded food made of minced meat. The term "piece of meat" as used herein is meant to indicate a relatively large (e.g., surface area of not less than 1 $cm^2$) meat cut from a raw meat such as beast meat. Examples of such a piece of meat include steak meat, roast meat, meat to be fried without coat, meat to be fried, and meat for teruyaki (meat grilled with sweet sake and sugar).

The meat modifier of the present invention can exert its effect when a meat is cooked. The effect is not restricted by any cooking method such as baking, frying, boiling and steaming. The meat modifier of the present invention can exert its effect on any cooking method, remarkably on baking and frying. Examples of meat dishes to which the meat modifier of the present invention can be applied include dishes of relatively large piece of meat or fish such as roast meat, steak, fried cutlet, meat fried without coat, tatsutaage (meat fried with dogtooth violet starch kneaded with sweet sake and sugar), curry, stew, shabu-shabu (boiled meat served with a sauce), roast fish (including kabayaki (spitchcock)) and meunière, and molded meet food made of minced meat such as hamburger, meatball, meat loaf, fried meat cake, gyoza (fried dumpling stuff with minced pork), shao-mai, won ton (Chinese flour dumpling with pork in them, served in soup), harumaki and meat bun.

The meat modifier of the present invention can be applied to frozen meat product, refrigerated meat product or meat product which can be stored at normal temperatures such as retorted food or molded minced meat food in these forms. The meat product containing pieces of meat processed with the meat modifier of the present invention or the molded food made of minced meat processed with the meat modifier of the present invention may be served in cooked form (cooked food) or may be cooked shortly before served (uncooked food). In some detail, the meat food to be served in cooked form may be processed with the meat modifier of the present invention during cooking. On the other hand, the meat food to be cooked shortly before served may have the meat modifier of the present invention adhered to act on the meat during cooking before served. The food product containing a meat processed with the meat modifier of the present invention can remain tender and juicy and thus can be served with good flavors even after storage. Examples of the meat food containing a meat processed with the meat modifier of the present invention include fried cutlet, karaage, curry, hash, stew, nikujaga (potato cooked with meat), subuta (sweet-and-sour pork), fried saurel, fried salmon, fried white fish (e.g., cod, flatfish, sillaginoid), plaice fried with coat, and kabayaki. Examples of the molded food made of minced meat include hamburger in any form such as frozen, refrigerated or retorted form.

Examples of the formulation of the meat modifier of the present invention comprising a succinic ester composition and specific examples of its recipe will be given below. Even if these formulations comprise a diacetyltartaric ester composition contained therein instead of succinic ester composition, they can be prepared in the same manner. The figures given below are parts by weight.

(1) Frying powder (for karaage (food fried without coat)) composition

| Flour (low grade flour) | 55 |
|---|---|
| Corn starch | 10 |
| Powdered sugar | 3.5 |
| Sodium chloride | 11 |
| Nonfat milk | 2 |
| Powdered soy sauce | 5 |
| Sodium glutaminate | 2.5 |
| Spice powder | 1 |
| Succinic ester composition | 10 |
| Total | 100 |

Example of recipe: 50 g of chicken is sprinkled with from 5 to 10 g of frying powder, and then fried.

The amount of the succinic ester composition to be used in the foregoing cook is preferably from 0.25 to 50% by weight, more preferably from 0.5 to 30% by weight.

(2) Cooking oil composition

| Corn salad oil | 95 |
|---|---|
| Succinic ester composition | 5 |
| Total | 100 |

Example of recipe: The cooking oil is poured into a frying pan in an amount of from 10 to 25 g per 100 g of sliced meat, and then heated. The meat is then fried with the cooking oil.

The amount of the succinic ester composition to be used in the foregoing cook is preferably from 0.2 to 50% by weight, more preferably from 0.4 to 30% by weight.

(3) Edible oil composition

| Soybean hardened oil (m.p. 34° C.) | 40 |
|---|---|
| Palm oil | 15 |
| Soybean oil | 20 |
| Succinic ester composition | 20 |
| Garlic powder | 2 |
| Pepper powder | 2 |
| Onion oil | 1 |
| Total | 100 |

Example of recipe: The plastic fatty oil is poured into a frying pan in an amount of from 20 to 40 g per 200 g of steak meat, and then heated and melted. The meat is then fried.

The amount of the succinic ester composition to be used in the foregoing cook is preferably from 0.25 to 50% by weight, more preferably from 0.5 to 30% by weight.

(4) Dipping sauce for roast

| Soy sauce | 27 |
|---|---|
| Sugar | 21 |
| Sweet sake | 18 |
| Thick malt syrup | 7 |
| Sodium chloride | 4.5 |
| Sodium glutaminate | 2 |
| Beef essence | 2 |
| Spice | 3 |
| Apple juice (5-fold concentrated) | 5 |
| Xanthane gum | 0.5 |
| Succinic ester composition | 10 |
| Total | 100 |

Example of recipe: 50 g of a meat to be grilled is mixed with from 5 to 15 g of the foregoing sauce, and then grilled.

The amount of the succinic ester composition to be used in the foregoing cook is preferably from 0.2 to 50% by weight (more preferably from 0.4 to 30% by weight).

The present invention will be further described in the following examples, but the present invention should not be construed as being limited thereto.

EXAMPLE 1-1

(Separation of protease PF-1-producing strain KSM-PF1)

A small amount of miso (soybean paste) was scratched off a commercially available pork pickled in miso, and then suspended in sterilized water. The suspension was properly diluted, inoculated into a skim milk agar culture medium, and then cultured at a temperature of 30° C. for 1 to 2 days. The agar culture medium was obtained by adding to a commercially available SCD agar culture medium (Nihon Pharmaceutical Co.) 0.5% of skim milk. The colony in which halo had occurred was then processed in accordance with an ordinary method to obtain a uniform protease-producing Bacillus sp. (KSM-PF1).

(Production of protease PF-1)

The Bacillus sp. (KSM-PF1) thus obtained was inoculated into an SCD culture medium (Nihon Pharmaceutical Co.), and then subjected to submerged-culture with stirring in a 5-l jar fermentor (3 l medium) at a temperature of 30° C. for 20 hours. The culture solution was then subjected to centrifugation to obtain 2.8 l (1.2 units (hereinafter referred to as "U")/ml) of a supernatant solution. The supernatant solution was sterilized by an MF membrane (0.22 µ), desalted and concentrated by a UF membrane, and then. lyophilized to obtain 6.1 g of an enzyme powder.

EXAMPLE 1-2

(Separation of protease-producing strain KSM-PF2 and production of protease PF-2)

A protease-producing Bacillus sp. KSM-PF2 was obtained in the same manner as in Example 1-1 except that a commercially available beef pickled in miso was used instead of the commercially available pork pickled in miso. The Bacillus sp. (KSM-PF2) thus obtained was inoculated into a culture medium for producing PF-2 (2.0% glucose, 0.5% yeast extract, 2.0% fish meat extract, 1.5% amino acid solution and 0.1% $Na_2CO_3$), and then subjected to submerged-culture with stirring in a 5-l jar fermentor (3 l medium) at a temperature of 30° C. for 20 hours. The culture solution was then subjected to centrifugation to obtain 2.6 l (4.5 U/ml) of a supernatant solution. The supernatant solution was sterilized by an MF membrane (0.22 µ), desalted and concentrated by a UF membrane, and then lyophilized to obtain 5.2 g of an enzyme powder.

EXAMPLE 2

(Purification and properties of PF-1)

A crude enzyme solution (540 U) obtained by dissolving the powdered enzyme PF-1 in distilled water was passed through a DEAE-Toyopearl® column which had been equilibrated with a 10 mM phosphoric acid buffer (pH 6.5), and then eluted with the same buffers containing 0 to 0.4M sodium chloride. The active fraction was concentrated by an ultrafilter, and then subjected to gel filtration chromatography by Sephadex-G75® column which had been equilibrated with a 20 mM tris buffer (pH 8.0). The active fraction which had so far been obtained (192 U) was measured for properties of PF-1 in accordance with the following methods.

(Purification and properties of PF-2)

A crude enzyme solution (408 U) obtained by dissolving the powdered enzyme PF-2 in distilled water was passed through a DEAE-Toyopearl® column which had been equilibrated with a 10 mM phosphoric acid buffer (pH 7.5), and then washed with the same buffer to recover a non-adsorbent active fraction (351 U). The active fraction was concentrated by an ultrafilter, and then subjected to gel filtration chromatography by Sephadex-G75® column which had been equilibrated with the same buffer as used above in an amount of 202 U. The active fraction which had so far been obtained (147 U) was measured for properties of PF-2 in accordance with the following methods.

(1) The molecular weight was determined by sodium dodecylsulfate (SDS)-polyacrylamide gel electrophoresis.

(2) The isoelectric point was determined by the isoelectric point electrophoresis method. As the amphoteric carrier for polyacrylamide gel there was used Biolite available from BIO-RAD Corp.

(3) In order to determine the optimum temperature, 0.2 U of PF-1 or PF-2 was added to a 0.1M phosphoric acid buffer (pH 7.0). The reaction mixture was then reacted at a temperature of from 20° C. to 70° C. The optimum temperature is defined by the temperature at which the highest activity is attained.

(4) In order to determine the optimum pH value, 0.2 U of PF-1 or PF-2 was added to 0.1M buffers having various pH values. These reaction mixtures were then reacted at a temperature of 40° C. For the pH range of from 4.0 to 6.0, a citric acid buffer was used. For the pH range of from 6.0 to 8.0, a phosphoric acid buffer was used. For the pH range of from 7.5 to 9.0, a tris buffer was used. For the pH range of from 9.0 to 10.0, a glycin-NaOH buffer was used. The optimum pH value is defined by the pH value at which the highest activity is attained.

(5) In order to determine the stabilization temperature, the sample was allowed to stand at various temperatures under the same conditions as used in the optimum temperature for 20 minutes. A substrate was then added to the sample. The residual activity at 40° C. was compared with the activity before processing. The stabilization temperature is defined by the temperature at which the residual activity is not less than 80% of the activity before processing.

(6) In order to determine the stabilization pH value, the engine was added to the buffers under the same conditions as used in the optimum pH value. The reaction mixtures were then allowed to stand at a temperature of 30° C. for 20 minutes. A phosphoric acid buffer having a pH value of 7.0 and a substrate were then added to the reaction mixtures. The residual activity of these samples were compared with the activity before processing. The stabilization pH value is defined by the pH value at which the residual activity is not less than 80% of the activity before processing.

(7) In order to determine the effect of inhibitor and metal, 0.2 U of PF-1 or PF-2 was added to 0.1 M tris buffers (pH 7.0) to which inhibitors and metallic salts as listed below had been added in such an amount that the final concentration as mentioned therewith was reached. The reaction mixtures were then processed at a temperature of 30° C. for 20 minutes. The residual activity of these samples were then compared with that of controls which had been processed in the same manner as above except that no inhibitors or metallic salts were added. The activity was determined relative to that of the control as 100. When the relative activity is remarkably low, an inhibiting effect can be recognized.

| Inhibitor and metallic salt | PF-1 | PF-2 |
| --- | --- | --- |
| DFP | 5 mM 125% | 5 mM 100% |
| PNSF | 5 mM 124% | 5 mM 80% |
| EDTA | 5 mM 45% | 5 mM 30% |
| DTT | 5 mM 70% | 5 mM 81% |
| Pepstatin | 5 mM 108% | 5 mM 100% |
| Leupepsin | 5 mM 82% | 5 mM 91% |
| Monoiodoacetic acid | 5 mM 105% | 5 mM 100% |
| $CaCl_2$ | 10 mM 104% | 10 mM 76% |
| $HgCl_2$ | 10 mM 40% | 10 mM 62% |
| $FeCl_2$ | — | 10 mM 28% |
| $FeCl_3$ | 10 mM 98% | 10 mM 9% |
| $CoCl_2$ | 10 mM 103% | 10 mM 78% |
| $CuCl_2$ | 10 mM 37% | 10 mM 20% |
| $ZnCl_2$ | 10 mM 88% | 10 mM 58% |
| $NiCl_2$ | 10 mM 92% | 10 mM 28% |
| $MgCl_2$ | 10 mM 107% | 10 mM 74% |
| $MnCl_2$ | 10 mM 103% | 10 mM 62% |

The properties of PF-1 and PF-2 based on the foregoing measurements will be given below.

| | | PF-1 | PF-2 |
| --- | --- | --- | --- |
| (1) | Molecular weight | 55,000 | 30,000 |
| (2) | Isoelectric point | pI6.5 | near pI9.0 |
| (3) | Optimum temperature | 40° C. | 50° C. |
| (4) | Optimum pH | pH 7.7 | pH 6.5–7.5 |
| (5) | Stabilization temperature | 40° C. or lower | 30° C. or lower |
| (6) | Stabilization pH | pH 6.0–8.0 | pH 6.5–9.5 |
| (7) | Inhibitor | EDTA, $Hg^{2+}$, $Cu^{2+}$ | EDTA, $Cu^{2+}$, $Fe^{3+}$, $Ni^{2+}$ |

It can be confirmed from the foregoing features that the activity of these enzymes are inhibited by EDTA, which is a chelating agent. Further, since the optimum pH value is in the neutral range, both PF-1 and PF-2 are neutral metalloproteases.

EXAMPLE 3

(Meat tenderization test)

The enzyme powders PF-1 and PF-2 thus obtained were subjected to meat tenderization test as follows:

As the meat to be tested there was used a low grade round (100 g) imported from Australia. The meat was sliced to 5-mm thick pieces by a meat slicer. Prominent strings were removed. About 20 g of the sliced meat was then molded. The molded meat was uniformly sprinkled with the enzyme powder, covered with a wrap, and then allowed to stand at room temperature (20° C.) for a predetermined period of time. The meat thus processed was then grilled over a 200° C. hot plate for 1 minute on one side and for 45 seconds on the other side. The meat thus grilled was then cut into 3-cm wide strips. The strips were then measured for shear force value (SFV) by means of a meat shear (Warner Bratzler Type 3000, available from Warner Bratzler Corp.). As comparative enzymes, a papain powder (available from Amano Co., Ltd.) and an elastase powder (reagent available from Sigma Co., Ltd.) were subjected to the same meat tenderization test as mentioned above. The results are set forth in FIG. 1.

Figure 1:
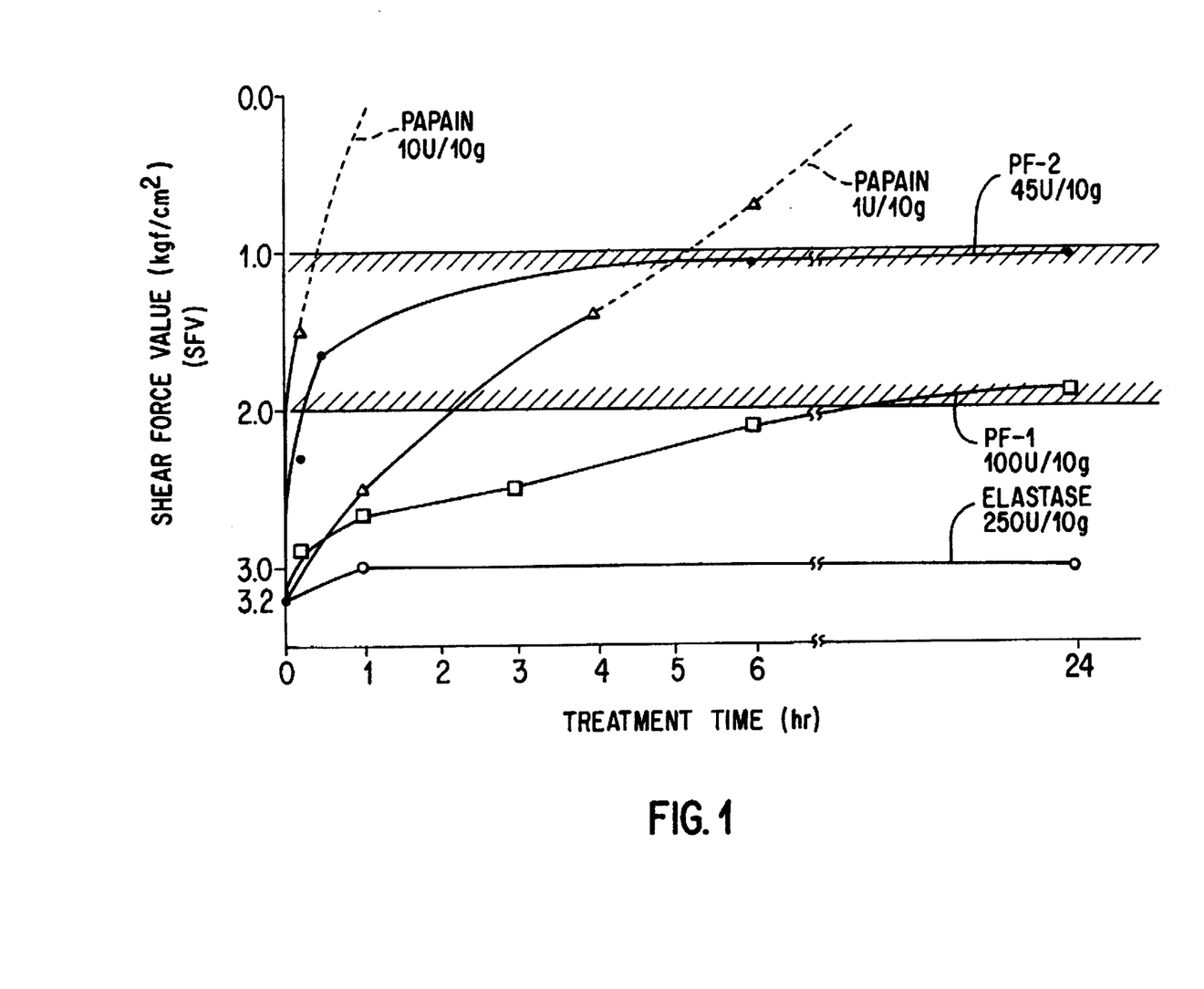
FIG. 1 is a graph illustrating the shear force value of a meat product obtained by processing a 5-mm thick meat with various proteases and then calcining the meat.

The results shown in FIG. 1 demonstrate that when the enzyme powder PF-1 according to the present invention is used (when a meat is processed with an enzyme in an amount of 100 U per 10 g), a proper tenderizing effect can be exerted in several hours (shear force value (SFV): 1 to 2 kgf/cm$^2$ (corresponding to 31 to 63% of the shear force value of the unprocessed meat)), and this state remains for 24 hours. Further, when the enzyme powder PF-2 according to the present invention is used (when a meat is processed with an enzyme in an amount of 45 U per 10 g), a proper tenderizing effect can be exerted in 30 minutes, and this state remains for 24 hours.

On the other hand, when the papain powder as a comparative enzyme is used (when a meat is processed with an enzyme in an amount of 10 U or 1 U per 10 g), an overtenderizing effect can be recognized in several hours in any case. When the elastase powder is used (when a meat is processed with an enzyme in an amount of 250 U as calculated in terms of elastin decomposition activity in accordance with the reagent indication), some tenderizing effect can be attained in 24 hours but a proper tenderness cannot be obtained.

EXAMPLE 4

(Meat tenderization test)

The foregoing enzyme powders PF-1 and PF-2 were subjected to meat tenderization test in the same manner as in Example 3.

The same meat as used in Example 3 was sliced perpendicular to muscular fibers to 15-mm thick pieces by a meat slicer. A maximum homogeneous portion of the sliced meat was molded into an about 30 g rod. The molded meat was uniformly sprinkled with the enzyme powder, covered with a wrap, and then allowed to stand at room temperature (20° C.) for a predetermined period of time. The meat thus processed was then grilled over a 200° C. hot plate for 3 minutes on each side. The meat thus grilled was cut into 2-cm wide strips which were then measured for shear force value in the same manner as in Example 3. As comparative enzymes, the same papain powder (available from Amano Co., Ltd.) and elastase powder (reagent available from Sigma Co., Ltd.) as used in Example 3 were subjected to the same meat tenderization test as mentioned above. The results are set forth in FIG. 2.

Figure 2:
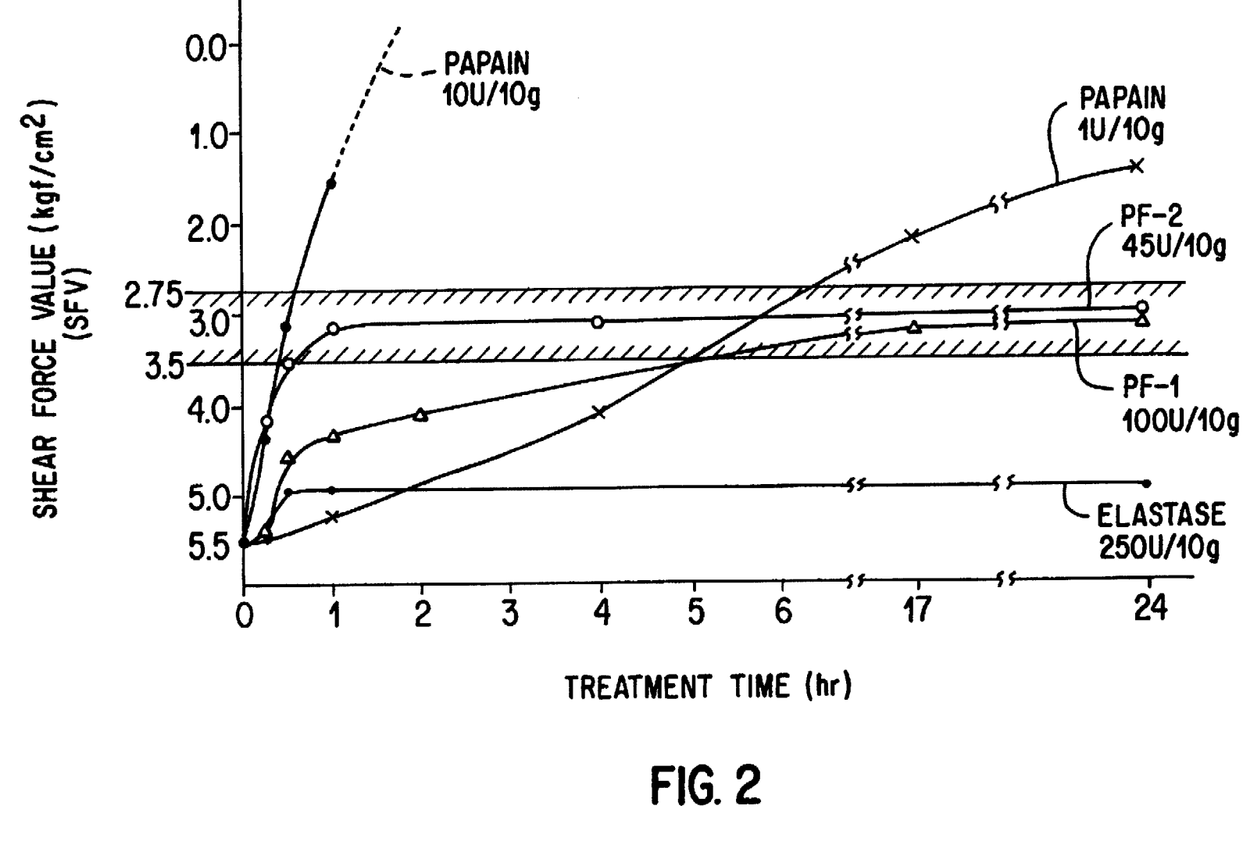
FIG. 2 is a graph illustrating the shear force value of a meat product obtained by processing a 15-mm thick meat with various proteases and then calcining the meat.

As shown in FIG. 2, the same results as obtained in Example 3 (FIG. 1) were obtained. In some detail, when the enzyme powder PF-1 according to the present invention is used (when a meat is processed with an enzyme in an amount of 100 U per 10 g), a proper tenderizing effect can be exerted in several hours (shear force value (SFV): 2.75 to 3.5 kgf/cm$^2$(corresponding to 50 to 64% of the shear force value of the unprocessed meat)), and this state remains for 24 hours. Further, when the enzyme powder PF-2 according to the present invention is used (when a meat is processed with an enzyme in an amount of 45 U per 10 g), a proper tenderizing effect can be exerted in 30 minutes, and this state remains for 24 hours.

On the other hand, when the papain powder as a comparative enzyme is used (when a meat is processed with an enzyme in an amount of 10 U or 1 U per 10 g), an overtenderizing effect can be recognized in several hours in any case. When the elastase powder is used (when a meat is processed with an enzyme in an amount of 250 U as calculated in terms of elastin decomposition activity in accordance with the reagent indication), some tenderizing effect can be attained in 24 hours but a proper tenderness cannot be obtained.

The foregoing results demonstrate that the proteases PF-1 and PF-2 according to the present invention can exert a proper tenderizing effect in several hours when the thickness of the meat is either 5 mm or 15 mm and show no overtenderizing effect in 24 hours. Further, PF-2 can exert a proper tenderizing effect earlier (in 1 hour) than PF-1 in a less amount than PF-1. On the other hand, papain shows an overtenderizing effect in several minutes to scores of minutes when used in a large amount. When used in a reduced amount, the enzyme can exert a proper tenderizing effect in an extended period of time but shows an overtenderizing effect in several hours. Elastase cannot exert an effect of properly tenderizing the meat.

Samples of the meat modifier, and other examples and comparative examples will be described hereinafter.

[Preparation of ester composition]

Sample A

As Sample A there was used a monoglyceride succinate (ester composition with a $C_{16-18}$ (mainly $C_{18}$) saturated monoglyceride to succinic acid mixing ratio of 1:1; Step SS, available from Kao Corp.). This ester composition had an acid value of 110. The foregoing monomer/polymer molar ratio of the ester composition was 82/18 and the amount of free acids was 2.1% by weight.

Sample B

Sample A was steamed at a temperature of 125° C. for 1 hour to obtain Sample B. Sample B had an acid value of 100. The foregoing monomer/polymer molar ratio of Sample B was 73/27 and the amount of free acids was 1.8% by weight.

Sample C

Sample A was washed three times with water in an amount of 5 times that of Sample A to obtain Sample C. Sample C had an acid value of 98. The foregoing monomer/polymer molar ratio of Sample C was 82/18 and the amount of free acids was 1.2% by weight.

Sample D

Sample A was steamed at a temperature of 150° C. for 1 hour to obtain Sample D. Sample D had an acid value of 85. The foregoing monomer/polymer molar ratio of Sample D was 64/36 and the amount of free acids was 0.9% by weight.

Sample E

Sample A was steamed at a temperature of 175° C. for 1 hour to obtain Sample E. Sample E had an acid value of 62. The foregoing monomer/polymer molar ratio of Sample E was 52/48 and the amount of free acids was 0.8% by weight.

Sample F

Sample A was steamed at a temperature of 200° C. for 1 hour to obtain Sample F. Sample F had an acid value of 30. The foregoing monomer/polymer molar ratio of Sample F was 30/70 and the amount of free acids was 0.6% by weight.

Sample G

Sample G was obtained by reacting $C_{16-18}$ (mainly $C_{18}$) saturated monoglyceride whose water content was adjusted to 0.1% by weight, with succinic anhydride at 90° C. for 1 hour. Sample G had an acid value of 115. The foregoing monomer/polymer molar ratio of Sample G was 90/10 and the amount of free acids was 1.3% by weight.

Sample H

As Sample H there was used a monoglyceride diacetyltartrate (Poem W-10, available from Riken Vitamin Co., Ltd.). Sample H had an acid value of 120 and the amount of free acids was 3.5% by weight.

Sample I

Sample H was steamed at a temperature of 125° C. for 1 hour to obtain Sample I. Sample I had an acid value of 98 and the amount of free acids was 1.9% by weight.

Sample J

Sample H was washed three times with water in an amount of 5 times that of Sample H to obtain Sample J. Sample J had an acid value of 90 and the amount of free acids was 1.5% by weight.

Sample K

Sample H was steamed at a temperature of 150° C. for 1 hour to obtain Sample K. Sample K had an acid value of 80 and the amount of free acids was 1.4% by weight.

Sample L

Sample H was steamed at a temperature of 175° C. for 1 hour to obtain Sample L. Sample L had an acid value of 62 and the amount of free acids was 1.3% by weight.

Sample M

Sample H was steamed at a temperature of 200° C. for 1 hour to obtain Sample M. Sample M had an acid value of 33 and the amount of free acids was 1.2% by weight.

COMPARATIVE EXAMPLE 1

About 0.25 g of Sample A in powder form was spayed over 50 g of 5-mm thick Australian round to be grilled. The meat thus processed was then grilled over a 200° C. hot plate.

COMPARATIVE EXAMPLE 2

The meat was grilled in the same manner as in Comparative Example 1 except that Sample H was used instead of Sample A.

COMPARATIVE EXAMPLE 3

The meat was grilled in the same manner as in Comparative Example 1 except that Sample A was not used.

EXAMPLES 5 TO 10

The meat was grilled in the same manner as in Comparative Example 1 except that Samples B to G were used instead of Sample A, respectively.

EXAMPLES 11 TO 15

The meat was grilled in the same manner as in Comparative Example 1 except that Samples I to M were used instead of Sample A, respectively.

[Evaluation of meat modifier and meat product processed therewith]

The grilled meats thus obtained were organoleptically evaluated by 20 panelists. For the organoleptical evaluation, the meat foods obtained in the foregoing examples and Comparative examples were compared in "tenderness" and "juiciness". The evaluation was made relative to Comparative Example 3 (unprocessed). Three levels "definitely tenderer (or more juicy)", "slightly tenderer (or more juicy)", and "same" were used. The three levels were represented by X, Y and Z, respectively.

Further, the grilled meats were measured for physical properties to evaluate the tenderness thereof. The tenderness of the meat was represented by shear stress determined by a meat shear (available from Warner Bratzler Corp.). The smaller the shear stress is, the more is the tenderness of the meat.

The flavor of the grilled meats were relatively evaluated in the same manner as above (X (good), Y (same), Z (poor)).

The results are set forth in Table 1.

TABLE 1

| | | Meat tenderizing effect | | |
|---|---|---|---|---|
| | Sample | Organoleptic evaluation | Shear stress (kg) | Flavor |
| Comparative Example 3 | Unprocessed | Z | 3.5 | X |
| Comparative Example 1 | A | X | 2.0 | Z |
| Example 5 | B | X | 2.0 | Y |
| Example 6 | C | X | 2.1 | X |
| Example 7 | D | X | 2.2 | X |
| Example 8 | E | X | 2.2 | X |
| Example 9 | F | Y | 2.5 | X |
| Example 10 | G | X | 1.9 | Y |
| Comparative Example 2 | H | X | 2.0 | Z |
| Example 11 | I | X | 2.1 | Y |
| Example 12 | J | X | 2.2 | Y |
| Example 13 | K | X | 2.5 | X |
| Example 14 | L | X | 2.5 | X |
| Example 15 | M | Y | 2.6 | X |

EXAMPLES 16 TO 23

A 5-mm thick Australian round to be grilled was sprinkled with Samples D, E, K and L in powder form in an amount of about 0.2 g per 50 g of the meat and protease derived from koji (enzyme content: 23%; available from Amano Pharmaceutical Co., Ltd.) or protease derived from Bacillus (Aloase AP-10, available from K.K. Yakult Honsha) in an amount of 0.05 g per 50 g of the meat. The meat thus processed was then grilled over a 200° C. hot plate.

These meat samples were then evaluated in the same manner as in the foregoing examples.

The results are set forth in Table 2.

TABLE 2

| | | | Meat tenderizing effect | | |
|---|---|---|---|---|---|
| Example No. | Sample | Protease | Organoleptical evaluation | Shear stress (kg) | Flavor |
| Example 16 | D | derived from koji | X | 1.6 | X |
| Example 17 | D | derived from Bacillus | X | 1.8 | X |
| Example 18 | E | derived from koji | X | 1.8 | X |
| Example 19 | E | derived from Bacillus | X | 1.8 | X |
| Example 20 | K | derived from koji | X | 1.9 | X |
| Example 21 | K | derived from Bacillus | X | 2.0 | X |
| Example 22 | L | derived from koji | X | 2.0 | X |
| Example 23 | L | derived from Bacillus | X | 2.2 | X |

The metalloprotease of the present invention can tenderize meats in a relatively short period of time but does not overtenderize the meats as the conventional enzyme. The metalloprotease of the present invention can process the meats to a proper tenderness and maintain this tenderness. Thus, the use of the metalloprotease of the present invention is not restricted by the added amount or processing time. Accordingly, the metalloprotease of the present invention is an enzyme which can be very easily used. In particular, the metalloprotease of the present invention can be advantageously used as a meat modifier. Meats processed with this enzyme can serve very easily.

The use of the meat modifier of the present invention can provide a tender and juicy meat. The meat modifier of the present invention is effective particularly for the cooking of a meat having a certain size. The use of the meat modifier of the present invention can also provide frozen (refrigerated) meat foods or other keepable meat foods which can remain tender and juicy and thus can be served with a good flavor even after storage.

While the invention has been described in detail and with reference to specific embodiments thereof, it will be apparent to one skilled in the art that various changes and modifications can be made therein without departing from the spirit and scope thereof.

What is claimed is:

1. A meat modifier composition, comprising an ester composition comprising a succinate monomer of formula (1) and a succinate polymer of formula (2):

(1)

(2)

wherein the molar ratio of said monomer to said polymer is 90:10 to 1:4;

said ester composition has an acid value of 30 to 120;

said ester composition has a free acid content of 1.5% by weight or less;

R is a $C_{12-22}$ group derived from a fatty acid; and n is an integer not less than 2.

2. The meat modifier of claim 1, wherein the ratio of said monomer to said polymer is 90:10 to 30:70.

3. The meat modifier of claim 1, wherein n is 2 to 4.

4. The meat modifier of claim 1, which is a powder.

5. The meat modifier of claim 1, which is in the form of a solution or dispersion in water or an aqueous liquid.

6. A composition, comprising the meat modifier of claim 1 and a meat.

7. The composition of claim 6, comprising 0.05 to 5% by weight of said meat modifier.

* * * * *